United States Patent

Hughes et al.

[11] Patent Number: 5,545,740
[45] Date of Patent: Aug. 13, 1996

[54] NITROSATION PROCESS

[75] Inventors: Mark J. Hughes, Welwyn, Hertfordshire; John Kitteringham, Hertford, Hertfordshire, both of England

[73] Assignee: SmithKLine Beecham, p.l.c., England

[21] Appl. No.: 284,617

[22] Filed: Aug. 11, 1994

[30] Foreign Application Priority Data

Feb. 20, 1992 [GB] United Kingdom ............... 9203688

[51] Int. Cl.⁶ ............... C07D 221/22; C07D 453/02; C07D 455/02
[52] U.S. Cl. ............... 546/112; 546/133; 546/138
[58] Field of Search ............... 546/133, 138, 546/112

[56] References Cited

U.S. PATENT DOCUMENTS 5,260,314  11/1993  Sauerberg et al. ............... 514/305

Primary Examiner—Alan L. Rothman
Attorney, Agent, or Firm—Linda E. Hall; Edward T. Lentz; Stephen A. Venetianer

[57] ABSTRACT

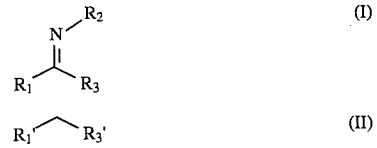

A process for preparing compounds of formula (I), by nitrosating compounds of formula (II), compounds of formula (I) having pharmaceutical activity.

6 Claims, No Drawings

NITROSATION PROCESS

CROSS REFERENCE

This application is a 371 of PCT/GB 93/00291 filed Feb. 11, 1993.

This invention relates to a process for the preparation of compounds having pharmaceutical activity.

EP-A-0392803 (Beecham Group p.l.c.) discloses certain azabicyclic compounds which enhance acetylcholine function via an action at muscarinic receptors within the central nervous system.

These compounds are therefore of potential use in the treatment and/or prophylaxis of dementia in mammals. Various preparative methods are also disclosed.

We have now developed an improved process for the preparation of one class of the compounds disclosed in EP-A-0392803.

The present invention provides process for the preparation of a compound of formula (I) or a pharmaceutically acceptable salt thereof:

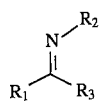

wherein $R_1$ represents

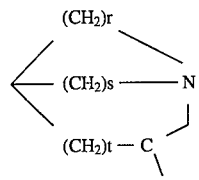

r represents an integer of 2 to 4, s represents 1 or 2 and t represents 0 or 1;

$R_2$ is a group $OR_4$, where $R_4$ is $C_{1-4}$ alkyl, $C_{2-4}$ alkenyl or $C_{2-4}$ alkynyl or a group $OCOR_5$ where $R_5$ is hydrogen or $R_4$; and $R_3$ is CN;

said process comprising nitrosating a compound of formula (II):

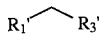

wherein $R_1'$ is $R_1$ or a group convertible thereto, and $R_3'$ is an electron withdrawing group, and thereafter converting the resulting =NOH group to =NR_2 wherein $R_2$ is as defined in formula (I), converting $R_1'$ and $R_3'$ when other than $R_1$ and $R_3$ to $R_1$ and $R_3$, and thereafter optionally forming a pharmaceutically acceptable salt.

Compounds of formula (I) are capable of existing in a number of stereoisomeric forms including geometric isomers such as syn and anti and, for certain compounds, enantiomers. The different stereoisomeric forms may be separated one from the other by the usual methods.

Compounds of formula (I) having two asymmetric centres which have the stereochemical configuration in which the group —C(R_3)=NR_2 and the (CH_2)_s bridge are on the same side of the plane of the molecule which contains both bridgehead atoms and the ring carbon atom bonded to the aforesaid group will hereinafter be referred to as having the exo configuration.

If desired, the compounds of formula (I) can be formed into acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

The term pharmaceutically acceptable salt encompasses solvates and hydrates. Thus where compounds of formula (I) or pharmaceutically acceptable salts thereof form solvates or hydrates, these also form an aspect of the invention.

Preferred combinations of (r,s,t) include (2,2,0), (2,1,1), (3,1,1), (2,1,0) and (3,1,0), most preferably (2,2,0).

The groups $R_4$ and $R_5$ in $R_2$ are preferably selected from methyl, ethyl, allyl and propargyl. Suitable values for $R_2$ include methoxy, ethoxy, allyloxy, propargyloxy and acetoxy, preferably methoxy.

Examples of suitable electron withdrawing groups include CN, $CO_2R$ and $CON(R)_2$ in which each R is independently H, $C_{1-8}$ alkyl, $C_{2-8}$ alkenyl, $C_{2-8}$ alkynyl, $C_{3-8}$ cycloalkyl, $C_{3-8}$ cycloalkyl $C_{1-4}$ alkyl or aryl $C_{1-4}$ alkyl, wherein aryl groups are selected from optionally substituted phenyl and naphthyl. Suitable examples of substituents on phenyl and naphthyl include one or more, for example 1 to 3, substituents selected from halo, hydroxy, $C_{1-4}$ alkoxy and $C_{1-4}$ alkyl. $R_3'$ is preferably CN.

The nitrosation of the compound of formula (II) may be carried out using a nitrosating agent such as an alkylnitrite, preferably a $C_{1-8}$ alkylnitrite such as t-butyl nitrite or, more preferably, iso-amyl nitrite and a base such as sodium ethoxide or, more preferably, potassium t-butoxide. Dimethylsulphoxide (DMSO) and tetrahydrofuran (THF) are suitable examples of solvents for the nitrosation.

The nitrosation results in a compound of formula (III):

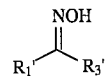

The =NOH group of the oxime of formula (III) may be converted to =NR_2 by conventional routes, for example compounds where $R_2$ is $OCOR_5$ can be made by acylation with an acylating agent such as an acyl halide, for example acetyl chloride. Compounds where $R_2$ is $OR_4$ can be made by alkylation with an alkylating agent such as methyltosylate (methyl p-toluene sulphonate) or an alkyl halide, for example methyl iodide. The alkylation is preferably carried out at a temperature of −20° C.–40° C., more preferably 0° C.–40° C., for example 18° C.–36° C., most preferably below 35° C.

$R_3'$ groups other than CN may be converted thereto conventionally, for example conversion, if necessary, to the primary amide followed by dehydration.

Examples of $R_1'$ groups other than $R_1$ include suitable azacyclic precursors which may be cyclised as described in, for example, EP 0392803.

The different steroisomeric forms of compounds of formula (I) may be separated one from the other by the usual methods, for example chromatographic methods. Enantiomers may be separated using chiral resolving agents such as (S)-(+)- and (R)-(−)-1,1'-binaphthyl-2,2'-diyl hydrogen phosphate, or chiral chromatography.

The invention also provides a process for preparing a compound of formula (III) which process comprises nitrosating a compound of formula (II) and thereafter converting $R_1'$ and $R_3'$ when other than $R_1$ and $R_3$ to $R_1$ and $R_3$ and thereafter optionally forming a salt.

Compounds of formula (II) can be prepared from compounds of formula (IV):

$$R_1 \diagup\hspace{-0.5em}\diagdown R_3' \quad\quad (IV)$$

by hydrogenation according to standard procedures.

The reduction of compounds of formula (IV) is preferably carried out by treating a methanolic solution of a compound of formula (IV) with hydrogen under pressure in the presence of Palladium on carbon as a catalyst.

Compounds of formula (IV) may be prepared conventionally, for example as described in EP 0414394, for example by reacting a compound of formula (V).

$$\begin{array}{c}(CH_2)r\\ \diagup\hspace{2em}\diagdown\\ \diagdown\hspace{-0.3em}-(CH_2)s\hspace{-0.5em}-\hspace{-0.5em}-N\\ \diagdown\hspace{2em}\diagup\\ (CH_2)t-C\\ \|\\ O\end{array} \quad (V)$$

with a phosphorus ylide of formula (VI) or (VII):

$$\begin{array}{c}R_a\\ \diagdown\hspace{0.2em}\oplus\hspace{0.5em}\ominus\\ R_b-P-CH-R_3'\\ \diagup\\ R_c\end{array} \quad (VI)$$

$$\begin{array}{c}R_aO\hspace{0.5em}O\\ \diagdown\hspace{0.2em}\|\hspace{0.5em}\ominus\\ P-CH-R_3'\\ \diagup\\ R_bO\end{array} \quad (VII)$$

in which Ra, Rb and Rc are independently $C_{1-6}$ alkyl, aryl or aralkyl and $R_3'$ is as defined above, to give a compound of formula (IVa):

$$\begin{array}{c}(CH_2)r\\ \diagup\hspace{2em}\diagdown\\ \diagdown\hspace{-0.3em}-(CH_2)s\hspace{-0.5em}-\hspace{-0.5em}-N\\ \diagdown\hspace{2em}\diagup\\ (CH_2)t-C\\ \|\\ CH-R_3'\end{array} \quad (IVa)$$

in which $R_3'$ is defined as for formulae (VI) and (VII) and thereafter, where necessary, converting $R_3'$ to CN.

The reaction of a compound of formula (V) with a phosphorus ylide of formula (VI) or (VII) which is equivalent to the conversion of a ketone to an olefin is known as a Wittig Reaction and may be carried out under conditions generally used for such reactions, in particular in the presence of a suitable base such as potassium t-butoxide or, more preferably, potassium hydroxide. Preferably a compound of formula (V) is reacted with a compound of formula (VII) in a Wadsworth Emmons reaction in which Ra and Rb are each $C_{1-6}$ alkyl, for example ethyl, and Z is cyano.

Where the $R_3'$ group is a carboxy derivative such as an alkoxycarbonyl group, it may be converted to a cyano group by conventional methods as described above, but preferably before hydrogenation or before nitrosation.

However, as stated above, $R_3'$ is preferably cyano and no conversion is necessary.

Alternatively, compounds of formula (IV) may be prepared by a Knoevenagel condensation (Zh. Obshch. Khim. 1962 32 2935, DE 2323303, CA 1014958 and U.S. Pat. No. 3,857,848).

Intermediates of formula (V) are known compounds (e.g. as described in Thill et al., J. Org. Chem., 1968, 33, 4376) or may be prepared analogously.

Intermediates of formula (VII) are known compounds or may be prepared by the standard Arbuzov reaction (Pure Appl. Chem. 9, 307–335 (1964)) or certain compounds of formula (VII) may be obtained commercially.

Intermediates of formula (VI) are known compounds or may be prepared by analogous methods. Certain compounds of formula (VI) may be obtained commercially.

The compounds of formula (I) are useful in therapy as described in EP-0392803.

The following Examples 1 and 2 illustrates the invention. Reference Examples 1 to 5 illustrate the preparation of intermediates.

REFERENCE EXAMPLE 1

To a stirred solution of 3-quinuclidinone (50 g; 0.309 mol) in water (250 ml) was added potassium hydroxide (17.35 g; 0.309 mol). After 15 minutes, diethyl cyanomethyl phosphonate (109.6 g; 0.619 mol) was added with a further 125 ml water. A solution of potassium hydroxide (52.07 g; 0.928 mol) in water (250 ml) was added dropwise over 30 minutes. The reaction was left overnight, saturated with NaCl then extracted into ethyl acetate (6×200 ml). The organic extracts were combined, dried over anhydrous $K_2CO_3$ and concentrated in vacuo to give 3-cyanomethylidene quinuclidine (44 g; 96%, (96% pure-gc)) as a 2:1 mixture of Z:E isomers.

REFERENCE EXAMPLE 2

A solution of the product of Reference Example 1 (44.2 g; 0.3 mol) in methanol (625 ml) containing ca 10% Pd/C (4 g) was stirred under hydrogen at 60 psi for 24 hrs. The suspension was filtered through Celite (trade mark), concentrated in vacuo and distilled under reduced pressure to give 3-cyanomethyl quinuclidine (36.2 g; 82%; bpt 118° C., 0.3 mmHg).

Example 1

To a stirred solution of potassium tert-butoxide (94.1 g; 0.84 mol) in tetrahydrofuran (250 ml) under nitrogen was added a solution of 3-(cyanomethyl)quinuclidine (60 g; 0.4 mol) in tetrahydrofuran (150 ml) during a period of 10 mins. The reaction was stirred for 10 minutes then cooled to 0° C. Isoamyl nitrite (51.5 g; 0.44 mol) was added at a rate such that the internal temperature did not exceed 25° C. The reaction was stirred for 20 minutes then diluted with dimethylsulphoxide (500 ml). Methyl tosylate (134 g; 0.72 mol) was added as a solution in dimethylsulphoxide (100 ml) at a rate such that the temperature did not exceed 35° C. After a further 20 minutes aqueous potassium carbonate (ca 5 wt % 500ml) was added and the reaction extracted with ethyl acetate (5×200 ml). The ethyl acetate extract was washed with 5 wt % aqueous potassium carbonate (4×250 ml), then saturated potassium carbonate (50 ml). The combined aqueous layers were re-extracted with ethyl acetate (500 ml) which was washed as above. The combined organic extracts were dried over anhydrous potassium carbonate (200 g) and concentrated in vacuo to give a brown oil containing ca. 80 wt % 3-[(cyano)(methoxyimino)methyl]quinuclidine as a 4:1 mixture of Z:E isomers, (47.4 g; 0.245 mol; 61%).

REFERENCE EXAMPLE 3

3-Quinuclidinone hydrochloride (6 kg, 37.1 mol) was added to water (30 L), the mixture was stirred for 5 minutes and to the resulting solution was added potassium hydroxide (2.08 kg, 31.5 mol) followed by diethyl cyanomethylphosphonate (13.26 kg, 74.9 mol) which was washed in with water (15 L). A solution of potassium hydroxide (6.26 kg, 94.8 mol) in water (30 L) was then added steadily over 1 hour during which time the temperature rose from 25° C. to a maximum of 48° C. The reaction was stirred for a further 1.5 hours and to the mixture was added salt (NaCl) (15 kg). The mixture was extracted with ethyl acetate (3×30 L) and the combined ethyl acetate extracts were dried over anhydrous potassium carbonate (8.7 kg). The potassium carbonate was filtered off, washed with ethyl acetate (10 L) and the combined ethyl acetate solutions were used directly in the next stage.

REFERENCE EXAMPLE 4

The solution of 3-(cyanomethylidine)quinuclidine from Reference Example 3 in ethyl acetate was added to a slurry of 10% palladium on charcoal (0.6 kg) in ethyl acetate (10 L). Hydrogen was introduced into the reaction vessel and the pressure was set at 20 psi. The mixture was stirred and the temperature was maintained below 30° C. until complete reaction was observed. (It may be necessary to add further amounts of catalyst to obtain complete reaction). The catalyst was removed by filtration and the filter bed washed with ethyl acetate (1×30 L and 1×35 L). The solution was concentrated, dried with anhydrous sodium sulphate (1 kg), filtered and concentrated to give an oil which was distilled under nitrogen at reduced pressure in two batches: (1.94 kg, collected in the range 109° C., 0.4 torr–108° C., 0.35 torr), (2.11 kg, collected in the range 112° C., 0.4 torr–110° C., 0.4 torr).

Example 2

To a stirred suspension of potassium t-butoxide (3.024 kg; 26.95 mole) in dry tetrahydrofuran (6.5 L) was added a solution of 3-(cyanomethyl)quinuclidine (Reference Example 4, 1.9 kg, 12.65 mol) in dry tetrahydrofuran (6 L) and this was washed in with dry tetrahydrofuran (0.5 L). The reaction mixture was cooled to 4° C. and isoamyl nitrite (1.964 kg, 16.76 mol) was added over 45 minutes during which time the temperature was maintained below 28° C. The reaction mixture was cooled to 0° C., diluted with dimethyl sulphoxide (32 L) and to this solution was added a solution of methyl p-toluene sulphonate (4.31 kg, 23.1 mol) in dimethylsulphoxide (5.5 L). The temperature was maintained in the range of 18° to 36° C. during the addition. The methyl p-toluene sulphonate was washed in with further dimethyl sulphoxide (1 L) and the reaction was stirred for a further 1 hour before quenching by the addition of 5% aqueous potassium carbonate solution (65 L) at below 30° C. The reaction mixture was extracted with ethyl acetate (3×26 L) and the combined ethyl acetate extracts were washed with 5% aqueous potassium carbonate solution (4×6.5 L) and saturated aqueous potassium carbonate solution (2×6.5 L), dried over anhydrous potassium carbonate (9 kg), filtered and concentrated to an oil (2.097 kg).

REFERENCE EXAMPLE 5

To a stirred solution of potassium tert-butoxide (4.0 ml of a 1.0M THF solution), cooled in an ice bath and under an atmosphere of helium, was added dropwise diethyl cyanomethylphosphonate (704 mg, 3.98 mmol) in THF (3 ml). On completion of the addition, the solution was cooled to −30° C. and 3-quinuclidinone (530 mg, 4.24 mmol) in THF (3 ml) was added dropwise. The mixture was stirred at ambient temperature for 18 h and diluted with $H_2O$ (7 ml), the pH was adjusted to 1 with concentrated .HCl and the mixture was extracted with ether (×2). The aqueous layer was made alkaline with solid $K_2CO_3$ and extracted exhaustively with ethyl acetate. The combined ethyl acetate extracts were dried over $MgSO_4$, filtered and evaporated to dryness to give the crude product as an off white oily solid (569.9 mg). The material can be purified by column chromatography (silica, elution with $CHCl_3/CH_3OH$ 20:1 v/v).

We claim:

1. A process for the preparation of a compound of formula (I) or a pharmaceutically acceptable salt thereof:

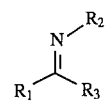

wherein $R_1$ represents

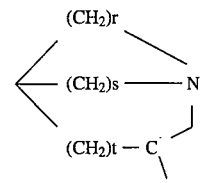

in which r represents an integer of 2 to 4, s represents 1 or 2 and t represents 0 or 1;

$R_2$ is a group $OR_4$, where $R_4$ is $C_{1-4}$alkyl, $C_{2-4}$alkenyl or $C_{2-4}$alkynyl or a group $OCOR_5$ where $R_5$ is hydrogen or $R_4$; and $R_3$ is CN;

said process comprising nitrosating a compound of formula (II) with a nitrosating agent in the presence of a base:

(II)

wherein $R_1'$ is $R_1$ or a group convertible thereto, and $R_3'$ is an electron withdrawing group, and thereafter converting the resulting =NOH group to =NR$_2$ wherein $R_2$ is as defined in formula (I), converting $R_1'$ and $R_3'$ when other than $R_1$ and $R_3$ to $R_1$ and $R_3$, and thereafter optionally forming a pharmaceutically acceptable salt.

2. A process according to claim 1 wherein (r,s,t) is (2,2,0) and $R_2$ is methoxy.

3. A process according to claim 2 wherein $R_3'$ is CN.

4. A process according to claim 3 wherein the nitrosating agent is an alkylnitrite.

5. A process according to claim 4 wherein the nitrosating agent is isoamyl nitrite.

6. A process according to claims wherein different stereoisomeric forms of the compound of formula (I) are separated one from the other.

* * * * *